United States Patent [19]

Baker et al.

[11] Patent Number: 4,476,708
[45] Date of Patent: Oct. 16, 1984

[54] FLOW CONTROLLER

[75] Inventors: Kenneth J. Baker, Moraga; Keith E. Buck, Alamo; Irving C. Chase, El Sobrante; Robert B. Fraser, El Cerrito; Clive Miles, Oakland, all of Calif.

[73] Assignee: Thoratec Laboratories Corporation, Berkeley, Calif.

[21] Appl. No.: 440,816

[22] Filed: Nov. 12, 1982

[51] Int. Cl.³ .................................................. G01N 31/00
[52] U.S. Cl. ........................................ 73/23; 137/114
[58] Field of Search .................. 73/23; 128/910, 719; 137/88, 114

[56] References Cited

U.S. PATENT DOCUMENTS

| | | | |
|---|---|---|---|
| 3,465,753 | 9/1969 | Levy | 73/23 |
| 3,482,431 | 12/1969 | Mochizuki | 73/23 |
| 3,566,673 | 3/1971 | Kogan | 73/23 |
| 3,701,280 | 10/1972 | Stroman | 73/23 X |
| 3,771,348 | 11/1973 | Villarroel | 73/23 |
| 3,824,168 | 7/1974 | Oswin | 128/719 X |
| 3,901,230 | 8/1975 | Henkin | 128/910 |
| 4,067,328 | 1/1978 | Manley | 128/910 X |
| 4,150,670 | 4/1979 | Jewett | 73/23 X |
| 4,249,528 | 2/1981 | Mathes | 128/910 X |
| 4,297,871 | 11/1981 | Wright | 73/23 |

Primary Examiner—Stephen A. Kreitman
Assistant Examiner—Vincent P. Kovalick
Attorney, Agent, or Firm—Lothrop & West

[57] ABSTRACT

A flow controller primarily for breathing gas analysis has a gas flow circuit leading from a breathing air inlet to a gas analyzer and to a vacuum source. Another gas is bled into the circuit between the breathing air inlet and a point upstream of the vacuum source. Such other gas is precluded from flowing upstream in the circuit toward the gas analyzer by making the intervening flow path or conduit of suitable dimensions to have a Péclet number at least equal to 4 and preferably greater than 4 and about 6.

10 Claims, 1 Drawing Figure

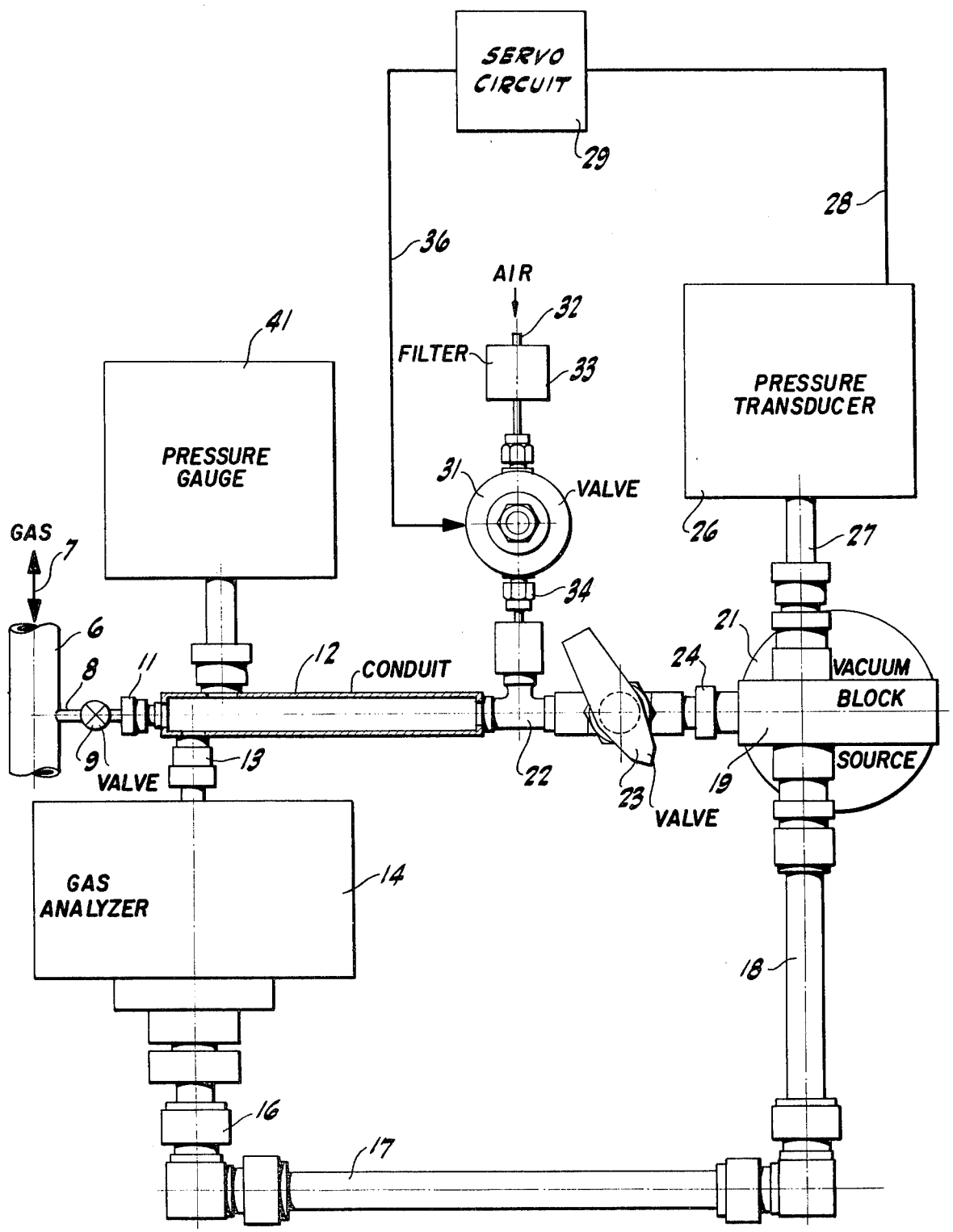

FLOW CONTROLLER

BRIEF SUMMARY OF THE INVENTION

A flow controller primarily for breathing gas analysis transmits the breathing gas from a source through an inlet to a branched circuit for flow to a vacuum device. The flow is both through a first branch and a parallel second branch. A gas analyzer is connected to the first branch near the inlet. Connected to the second branch is a pressure transducer controlling a variable leak of pressure adjusting air or other gas into the second branch at a predetermined location spaced downstream from the inlet. Molecules of air or other gas from the leak are prevented from flowing upstream in the first branch toward the inlet by a conduit between the predetermined location and the inlet, the conduit being formed to have a Péclet number of at least 4 and preferably of 6 or more.

PRIOR ART

The applicants are currently unaware of any prior art pertinent to the present disclosure.

BRIEF DESCRIPTION OF THE DRAWING

The FIGURE is a diagram, with some portions broken away and some portions in cross-section, showing a flow controller pursuant to the invention.

DETAILED DESCRIPTION

It is often desirable to monitor the gases; e.g. oxygen, utilized by patients being assisted in breathing when hospitalized or when being tested. These gases are sometimes referred to herein as "a gas". The monitoring is preferably during inhalation and exhalation in order to determine the components or constituencies of the involved gas. It is helpful to maintain a rigorous test procedure with an appropriate, accurate analyzer arranged so that variations in the breathing gas are not disruptive of the monitoring process, and arranged in such a way as to afford uniform or nearly uniform test conditions.

In order to provide such a test or controlled environment, there is disclosed, as an example, a breathing tube 6. This is connected at one end to the patient in any known way, such as by a face mask, and has a connection at the other end in accordance with standard practice. The gas flows through the breathing tube 6 in opposite directions at different times during the patient's breathing cycle, as indicated by the arrow 7.

To sample such gas or gases, there is provided a tube 8 intersecting the tube 6 at an appropriate point and preferably having a control valve 9 therein so that the flow area can be varied. The tube 8 leads through a connector 11 into a conduit 12 forming part of one circuit branch. A connector 13 opening at a first predetermined point into the conduit 12 is joined to a gas analyzer 14 of any appropriate sort. The analyzer in turn extends through connectors 16 to a tube 17 forming part of another circuit branch paralleling the conduit 12. The branches, including the conduit 12, and the tube 17, provide duplex paths for conjoint gas flow. The tube 17 is joined by a tube 18 to a block 19 open to a source 21 of vacuum or subatmospheric pressure, preferably any well-known vacuum pump, conveniently a two-stage pump. The conduit 12 at a second predetermined point connects through a tee 22 and a regulating valve 23 to a coupling 24. In turn, the coupling 24 joins to the block 19 and so is also in communication with the vacuum source 21. The end of the conduit 12, the tee 22, the valve 23, the coupling 24 and the block 19 afford a first circuit, branch, flow path or duct to the vacuum source. The conduit 12, the connector 13, the gas analyzer 14, the connectors 16, the tubes 17 and 18 and the block 19 afford a separate, second circuit, branch, flow path or duct to the vacuum source 21.

Also communicating with the block 19 and subject to the influence of the associated circuit branches is a pressure transducer 26 joined to the block through a pipe 27. The transducer 26 is effective to afford an electrical signal in a conductor 28, the signal corresponding to the pressure effective upon the transducer 26. The signal in the conductor 28 goes through a servo mechanism 29 effective to control a valve 31, preferably magnetically operated. The valve 31 is interposed between an inlet tube 32 open to the atmosphere and extending through a bacteria filter 33 to the inlet of the valve 31. The outlet 34 from the valve 31 is connected to the tee 22. Since the valve 31 is controlled by a signal from the transducer 26 through the conductor 28 and the servo circuit 29 and through a lead 36, the position of the valve 31 and flow from the atmosphere into the tee 22 and beyond is under the control of the pressure transducer 26.

Also engaging the conduit 12, preferably near the connector 13 of the gas analyzer, is a pressure transducer or gauge 41 indicating the instantaneous pressure within the tube 12.

Pursuant to the invention, the construction of the conduit 12 is of a special nature. The length and internal dimensions of the conduit 12 are such that the Péclet number for the conduit 12 is preferably about 6 or more and is greater than about 4. The Péclet number is a dimensionless number expressing the relationship of the magnitude of gas mass transport through the tube 12 by bulk flow due to gas velocity and by gas diffusivity. It is expressed as:

Péclet number = (VL/D) wherein
V = gas flow in cm/sec
L = characteristic flow path length in cm
D = mass diffusivity in cm²/sec In early work on the present device, it was noted that nitrogen used as a pressure compensating or make-up gas and entering through the inlet 32 into the tee 22 was diffusing upstream against the downstream-flowing breathing gas (oxygen), and so was contaminating the breathing gas in-flow into the gas analyzer 14. This caused misleading readings. A study of gas diffusion, and especially of mass diffusivity, ensued. An estimate of gas diffusivity can be made from the relationship:

$$D_{AB} = 0.0018583 \frac{\sqrt{T^3 \left( \frac{1}{M_A} + \frac{1}{M_B} \right)}}{P\sigma_{AB}^2 \Omega_{D,AB}} \text{ cm}^2/\text{sec}$$

wherein
T = temperature (T°K.) in degrees Kelvin
M = molecular weight
P = pressure in atmospheres
$\rho_{AB}$ = interaction distance between molecules in Angstroms
$\Omega_{D,AB}$ = a dimensionless relationship between temperature and the intramolecular field Using empirical information given in the reference Bird, Stewart and Lightfoot, "Transport Phenomena" (John Wiley & Sons, 1960), the values $\rho_{AB}$ and $\Omega_{D_{AB}}$ can be determined for oxygen and nitrogen. If T=298° K. and P=1 Torr or 1/760 atmosphere, it is determined that $D_{AB}$=165 cm²/sec.

With this evaluation, a representative distance (L) axially of the conduit 12 approximately between the center of the connector 13 and the center of the fitting or tee 22 is about 13 cm. The diameter of the conduit 12 in one instance is preselected as 0.375 inches. The flow rate is 5 ml/min at standard temperature and pressure. The pressure is 0.1 Torr, V is 89 cm/sec, the Péclet number is about 6.0, and there is then no upstream flow of contaminating gas.

The Péclet number can be chosen at any desired value, depending upon a corresponding relationship of the involved factors. In practice, if some contamination is tolerable, the Péclet number may be as low as about 4 or 5, but the value 6 has been found to be acceptable for no contamination under the disclosed circumstances. While the proportions and relationships can be arranged to result in even higher Péclet numbers; say, 10, there is no particular benefit so far as contamination is concerned above the value around 6. When the above-noted relationships are observed, there is produced an acceptable operation of the structure.

With the tube 6 connected and arranged as a natural or induced breathing line for an individual and with the valve 23 set at a selected value to afford the desired degree of resistance, and with the circuitry energized and the vacuum pump 21 operating, there is gas flow from the restricting valve 9 to the vacuum source 21 as well as a corresponding pressure drop. There is flow from the breathing tube 6 through the connector 13 and through the gas analyzer 14 because the analyzer is also connected through the tubes 17 and 18 and the block 19 to the vacuum source 21.

There is continuous flow into the gas analyzer so that the analyzer can afford an instantaneous, current indication of the breathing gas flowing into and through it. The pressure of the diverted gas is indicated by the monitor gauge 41. The pressure and the flow in the tube 6 may tend to vary substantially. This partly depends upon the connections thereto; that is, whether a patient alone is connected to the breathing tube, or whether a breathing device is also used.

The general gas flow is through the conduit 12 from left to right in the FIGURE and to the vacuum source. The rate of flow is regulated in part by the position and restriction of the variable valve 23. Flows from the branch containing the tube 12 and from the branch containing the conduit 17 and tube 18 merge within the block 19 and that pressure is communicated through the tube 27 to the pressure transducer 26. Variations therein furnish signals through the conductor 28 and the servo conduit 29 and the conductor 36 to the valve 31. This valve correspondingly opens and closes, at least partially, to vary the in-flow of atmospheric air (or other supplied gas) through the leak 32, the filter 33, and through the valve 31 into the tee 22.

The atmospheric in-flow is preferably such in amount that the pressure in the conduit 12, for example, is maintained as nearly as possible at a constant value. Some of this inflowing air passes through the valve 23 to the vacuum source 21. Some of this air tends to move by diffusion upstream or from the tee 22 toward the connector 13; that is, contrary to or opposite to the direction of flow of the incoming gas from the breathing tube 6. The conduit 12 under many circumstances and unless specially arranged is subject to gas flows simultaneously in two directions. One of the flows, due to pressure drop, is in a direction from the left in the FIGURE; say, from the connector 11, for example, toward the tee 22. The other flow is molecular diffusion flow toward the left in the FIGURE from the tee 22 toward the connector 11. The pressure drop flow and the molecular diffusion flow under some circumstances are acceptable, but under other circumstances they are highly deleterious in that atmospheric air, for example, flows into the gas analyzer and contaminates the breathing gas sample furnished to the gas analyzer from the tube 6, so obscuring or precluding accurate results.

Especially to prohibit or control such contamination by upstream molecular flow, the dimensions or configurations of the conduit 12 are carefully limited to afford a Péclet number as above described. Under the described circumstances, the molecular air diffusion upstream from the tee 22 toward the connector 11 is not greater than the downstream flow of breathing gas from the connector 11 toward the tee 22. Gas arriving at the tee 22 from the inlet tube 32 does not diffuse upstream through the conduit 12 and so cannot enter through the fitting 13 into the analyzer 14 and contaminate the breathing gas being tested and so cannot affect the results of the gas analyzer 14.

Thus, with this arrangement it is possible despite variations in velocity and pressure by the breathing gas from the breathing tube 6 to afford a remarkably accurate gas analysis in the analyzer 14 by maintaining appropriate pressure in and flow through the conduit 12 and without permitting contamination by other gas let in to adjust or maintain the internal pressure within the conduit 12.

We claim:

1. A flow controller comprising a source of gas to be analyzed, a vacuum source, a conduit, means for connecting one end of said conduit to said source of gas, means for connecting the other end of said conduit to said vacuum source, a duct, means for connecting one end of said duct to said one end of said conduit, means for connecting the other end of said duct to said vacuum source, a gas analyzer, means for connecting said gas analyzer to said one end of said conduit and to said vacuum source, means for admitting another gas to said conduit at a predetermined point between said one end of said conduit and said vacuum source, and means having a Peclet number of at least 4 incorporated in said conduit between said one end thereof and said predetermined point.

2. A flow controller as in claim 1 including means for restricting gas flow from said source of gas.

3. A flow controller as in claim 1 including means for obturating said conduit for restricting flow toward said vacuum source.

4. A flow controller as in claim 1 including a variable valve in said means for admitting another gas.

5. A flow controller as in claim 1 including a variable valve in said means for admitting another gas, and a pressure transducer subject to pressure in said conduit and effective to vary said variable valve.

6. A flow controller comprising a source of gas to be analyzed, said source being at a predetermined pressure, a source of pressure lower than said predetermined pressure, means defining a first flow path for conducting gas from said source of gas to said source of lower pressure, a gas analyzer connected into said first flow path at a first predetermined point, a second flow path for conducting gas from said source of gas to said source of lower pressure, means for admitting another gas to said second flow path at a second predetermined point between said first predetermined point and said source of lower pressure, said second flow path being unobstructed between said first predetermined point and said second predetermined point, and means for inhibiting flow of said other gas through said unobstructed portion of said second flow path from said second predetermined point toward said first predetermined point.

7. A flow controller as in claim 6 in which said inhibiting means permits flow of said gas to be analyzed from said source of gas toward said source of low pressure.

8. A flow controller comprising a source of gas to be analyzed, a gas analyzer, a vacuum pump, a conduit at one end open to said source of gas to be analyzed and to said gas analyzer and at the other end open to said vacuum pump, a source of another gas, means for conducting said other gas from said source into said conduit at a predetermined point between said one end and said other end, said conduit between said one end and said predetermined point being unrestricted and constructed to inhibit flow of said other gas in said conduit from said predetermined point to said one end.

9. A device as in claim 8 in which said conduit between said one end and said predetermined point has a Péclet number of at least 4.

10. A flow controller as in claim 8 in which said conduit between said one end and said predetermined point has a Péclet number of about 6.

* * * * *